(12) United States Patent
Lajarín Barquero

(10) Patent No.: US 10,835,706 B2
(45) Date of Patent: Nov. 17, 2020

(54) NEEDLE DEVICE FOR A NERVE BLOCK

(71) Applicants: Bartolomé Lajarín Barquero, Murcia (ES); Beatriz Castellón Hernández, Murcia (ES)

(72) Inventor: Bartolomé Lajarín Barquero, Murcia (ES)

(73) Assignees: Bartolomé Lajarín Barquero, Murcia (ES); Beatriz Castellón Hernández, Murcia (ES)

( * ) Notice: Subject to any disclaimer, the term of this patent is extended or adjusted under 35 U.S.C. 154(b) by 160 days.

(21) Appl. No.: 16/087,208

(22) PCT Filed: Feb. 14, 2017

(86) PCT No.: PCT/ES2017/070085
§ 371 (c)(1),
(2) Date: Sep. 21, 2018

(87) PCT Pub. No.: WO2017/162895
PCT Pub. Date: Sep. 28, 2017

(65) Prior Publication Data
US 2019/0105459 A1    Apr. 11, 2019

(30) Foreign Application Priority Data
Mar. 23, 2016   (ES) .................. 201630367 U

(51) Int. Cl.
*A61M 19/00* (2006.01)
*A61B 17/34* (2006.01)
(Continued)

(52) U.S. Cl.
CPC ............. *A61M 19/00* (2013.01); *A61B 17/34* (2013.01); *A61N 1/05* (2013.01); *A61N 1/0502* (2013.01);
(Continued)

(58) Field of Classification Search
CPC ... A61N 1/00; A61N 1/02; A61N 1/04; A61N 1/0502; A61N 1/0504; A61N 1/0551;
(Continued)

(56) References Cited

U.S. PATENT DOCUMENTS

| 3,682,162 A | 8/1972 | Colyer |
| 7,194,312 B2 | 3/2007 | Pajunk et al. |

(Continued)

FOREIGN PATENT DOCUMENTS

| EP | 0966922 A1 | 12/1999 |
| ES | 2197543 T3 | 1/2004 |

(Continued)

OTHER PUBLICATIONS

Braun. "Stimuplex Ultra 360." https://www.bbraun.com/en/products/b2/stimuplex-ultra-360.html, 2018, Printed from the Internet Oct. 16, 2018.

(Continued)

*Primary Examiner* — Jason E Flick
(74) *Attorney, Agent, or Firm* — The Webb Law Firm

(57) ABSTRACT

Provided herein is a needle device for a nerve block, which includes a gripping part having a longitudinal passage through which a liquid fluid flows, said liquid fluid also flowing through the inside of a needle aligned with the longitudinal passage. The device also includes a nerve stimulator through which electricity is transmitted to the needle. The gripping part includes a radial duct that intersects tangentially with the longitudinal passage, the radial duct having two opposite female couplings into either of which the nerve stimulator can be inserted, depending on whether the user is left-handed or right-handed.

11 Claims, 3 Drawing Sheets

(51) Int. Cl.
*A61N 1/05* (2006.01)
*A61B 17/00* (2006.01)
*A61B 5/04* (2006.01)

(52) U.S. Cl.
CPC ....... *A61B 5/04001* (2013.01); *A61B 17/3401* (2013.01); *A61B 2017/00424* (2013.01); *A61M 2230/08* (2013.01)

(58) Field of Classification Search
CPC .... A61N 1/05; H01R 13/025; H01R 2201/12; A61M 19/00; A61M 2230/08; A61B 17/34; A61B 17/3401; A61B 2017/00424; A61B 5/04001
See application file for complete search history.

(56) References Cited

U.S. PATENT DOCUMENTS

| | | | |
|---|---|---|---|
| 7,643,884 B2 | 1/2010 | Pond, Jr. et al. | |
| 7,715,925 B2 | 5/2010 | Hafer et al. | |
| 8,798,766 B2 | 8/2014 | Carrez et al. | |
| 2009/0012578 A1* | 1/2009 | Carrez | H01R 13/025 607/46 |

FOREIGN PATENT DOCUMENTS

| | | |
|---|---|---|
| ES | 2272680 T3 | 5/2007 |
| ES | 2333484 T3 | 2/2010 |
| ES | 1143259 U | 9/2015 |
| WO | 2006083729 A1 | 8/2006 |

OTHER PUBLICATIONS

Panjunk. "Single Shot Techniques." https://www.pajunk.com/c3view.php.?sid=5eVb8Y3F8Hlef8gVb31Vw84sV15Vbw5b558elg3f&ieb=1539623105&c3p=762&c3l=en, 2018, Printed from the Internet Oct. 16, 2018.

Vygon. "Visioplex—Bevel 30." https://www.vygon.com/catalog/visioplex_1213_006094103, 2018, Printed from the Internet Oct. 16, 2018.

Temena. "Nerve Blocks Under Ultrasound." https://temena.com/product-line/regional-anesthesia-analgesia/peripheral-nerve-blocks-under-ultrasound/#57c4130d61da7, 2018, Printed from the Internet Oct. 16, 2018.

Teleflex. "Arrow StimuQuik ECHO Echogenic Stimulating PNB Needle." https://www.teleflex.com/usa/product-areas/anesthesia/pain-management/peripheral-nerve-blocks/arrow-stimuquik-echo-echogenic-stimulating-pnb-needle/, 2018, Printed from the Internet Oct. 16, 2018.

* cited by examiner

SEC. A - A

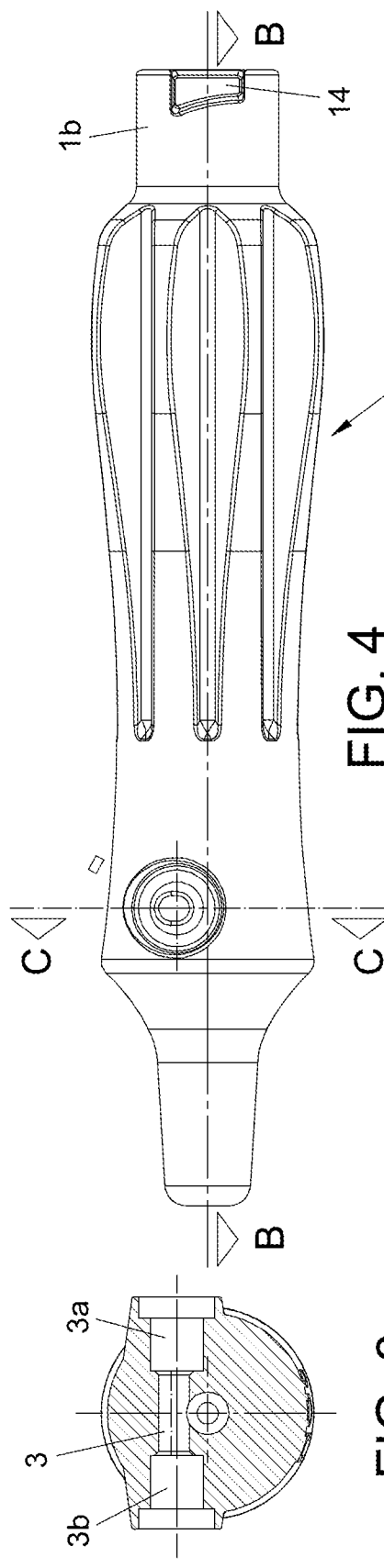
FIG. 4
FIG. 6
SEC. C - C
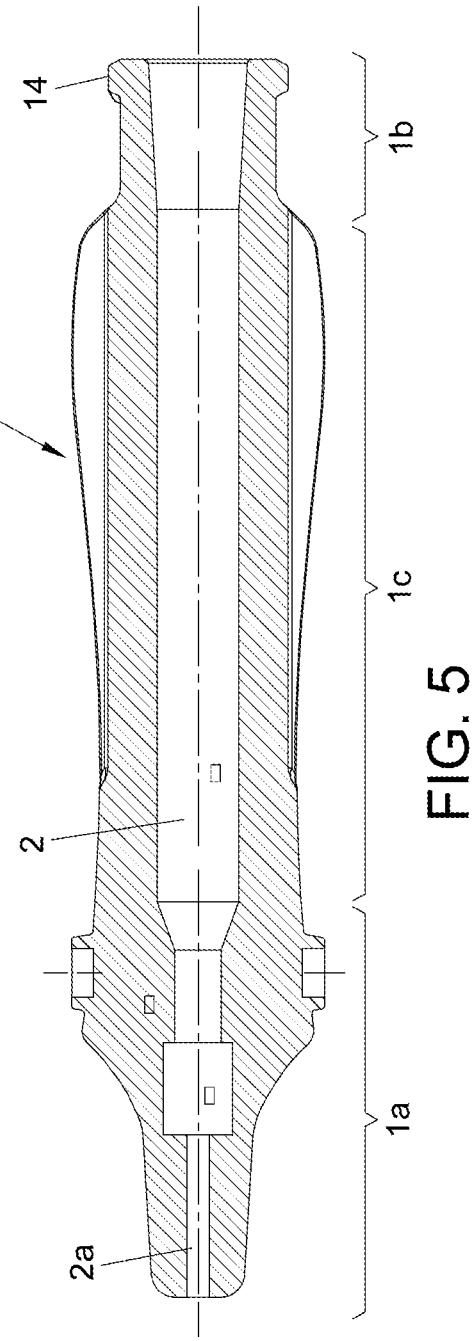
FIG. 5
SEC. B - B

NEEDLE DEVICE FOR A NERVE BLOCK

CROSS-REFERENCE TO RELATED APPLICATIONS

This application is the United States national phase of International Application No. PCT/ES2017/070085 filed Feb. 14, 2017, and claims priority to Spanish Patent Application No. U201630367 filed Mar. 23, 2016, the disclosures of which are hereby incorporated in their entirety by reference.

OBJECT OF THE INVENTION

The present invention, as expressed in the heading of this specification, relates to a needle device for a nerve block that allows a specific area of the body to be anesthetized by means of a peripheral nerve block. The process of administering the anesthesia consists of using a nerve stimulator to locate the nerves that control the sensitivity of an area where surgery will be carried out. Once the nerve has been located, a needle is inserted through the skin close to the nerve in order to inject the anesthetic fluid, thereby anesthetizing the area where the surgery will be carried out. The device of the invention allows for the nerve stimulator to be bilaterally connected, depending on whether the user is left-handed or right-handed. Furthermore, it must be noted that in the present invention, the nerve stimulator connects in a removable way.

Technical Problem to be Solved and Background of the Invention

Needle devices for a nerve block which generally comprise a gripping part having a longitudinal passage through which a liquid fluid flows, said liquid fluid also flowing through the inside of a needle aligned with the longitudinal passage, further comprising a nerve stimulator through which electric current is transmitted to the needle, are currently known.

The gripping parts of these needle devices have designs that are not very ergonomic, with a configuration that does not adapt well to the user's hand (the user being a specialist or anesthesiologist), and with this being the case, problems with precision during the handling of the needle device sometimes occur when inserting the needle through the skin of a patient.

On the other hand, the nerve stimulator is an element that is located in a specific area of the gripping part and without the possibility of being moved to another area, such that in this case, depending on whether the user is left-handed or right-handed, the location of said nerve stimulator may hinder and slow the application of the needle device, which can lead to a lack of precision during the application thereof.

The patent with publication number ES1143259 relates to needle for applying neuraxial anesthesia, comprising a first grip handle that supports a first tube, said first grip handle covered on the free end thereof by a mandrel.

The first grip handle comprises a semi-spherical lens on the upper central part for detecting the exit of cerebrospinal fluid. A rear part of said mandrel has a round form for better adapting to the user's hand and a slight upward inclination in order to be able to grab the needle form a worktable with just one hand.

DESCRIPTION OF THE INVENTION

With the aim of achieving the objectives and avoiding the drawbacks mentioned in the previous section, the invention proposes a needle device for a nerve block, which comprises a gripping part having a longitudinal passage through which a liquid fluid flows, said liquid fluid also flowing through the inside of a needle aligned with said longitudinal passage. The device of the invention also comprises a nerve stimulator through which electric current is transmitted to the needle.

The gripping part comprises a radial duct that intersects tangentially with the longitudinal passage, the radial duct having two opposite female couplings into either of which the nerve stimulator can be inserted, depending on whether the user is left-handed or right-handed.

Housed inside an anterior end section of the longitudinal passage of the gripping part is a cylindrical bushing made of conductive material, said cylindrical bushing being located in an area of confluence in which the longitudinal passage and the radial duct converge, and said cylindrical bushing has an axial hole into which an outer portion of the needle fits.

The nerve stimulator includes a deformable connector with an outer portion that comes into contact with the cylindrical bushing to transmit electric current to the needle when said nerve stimulator is inserted into one of the female couplings of the gripping part.

In one embodiment of the invention, said cylindrical bushing includes a radial nipple with which the outer portion of the deformable connector of the nerve stimulator makes contact. Said cylindrical bushing comprises a first cylindrical body with a greater diameter and a second cylindrical body with a smaller diameter, which integrates the radial nipple.

In one embodiment, the radial duct passage of the gripping part is located in a direction perpendicular to the direction of the longitudinal passage of the gripping part.

The gripping part comprises a revolution geometry with an centered outer section made up of a first grooved structure formed by an alternating succession of longitudinal protrusions and channels.

An anterior end section of the longitudinal passage of the gripping part has a narrowing where a section of the needle is adjusted, which is a continuation of the end portion of said needle embedded and fixed in the axial hole of the cylindrical bushing.

The gripping part comprises a rear portion that has facing protrusions, where, in said rear portion, an outer coupling of a connecting tube through which the liquid fluid flows is coupled with axial and rotational retention.

The nerve stimulator comprises an insertable head that on one end has a male element that by an elastic pull is embedded inside one of the female couplings of the gripping part. Said male element of the nerve stimulator has an annular protrusion that is complemented by an annular groove located inside one of the female couplings.

The insertable head of the nerve stimulator has a revolution geometry with an outer section made up of a second grooved structure formed by an alternating succession of longitudinal protrusions and channels.

The inclusion of the two opposite female couplings of the gripping part allows for a bilateral connection of the nerve stimulator, depending on whether the user is left-handed or right-handed. Furthermore, we must mention that in the present invention the nerve stimulator is connected in an removable way, such that the device of the invention can be used with or without the nerve stimulator, and furthermore, said nerve stimulator can be connected to the side that is most suitable to the user (specialist/anesthesiologist), depending on whether they are left-handed or right-handed.

It is also worth mentioning that the characteristic revolution geometry of the gripping part allows the device to rotate by means of the user's fingertips to thereby achieve a greater precision during the use of the device of the invention.

For the purpose of helping to make this specification more readily understandable, a set of drawings constituting an integral part of the same has been included below, wherein by way of illustration and not limitation the object of the invention has been represented.

BRIEF DESCRIPTION OF THE FIGURES

FIG. 4 shows an elevation view of a gripping part that makes up part of the device of the invention.

FIG. 5 shows a B-B cross-sectional view of FIG. 4.

FIG. 6 shows a C-C cross-sectional view of FIG. 4.

DESCRIPTION OF AN EXEMPLARY EMBODIMENT OF THE INVENTION

Figure 1:
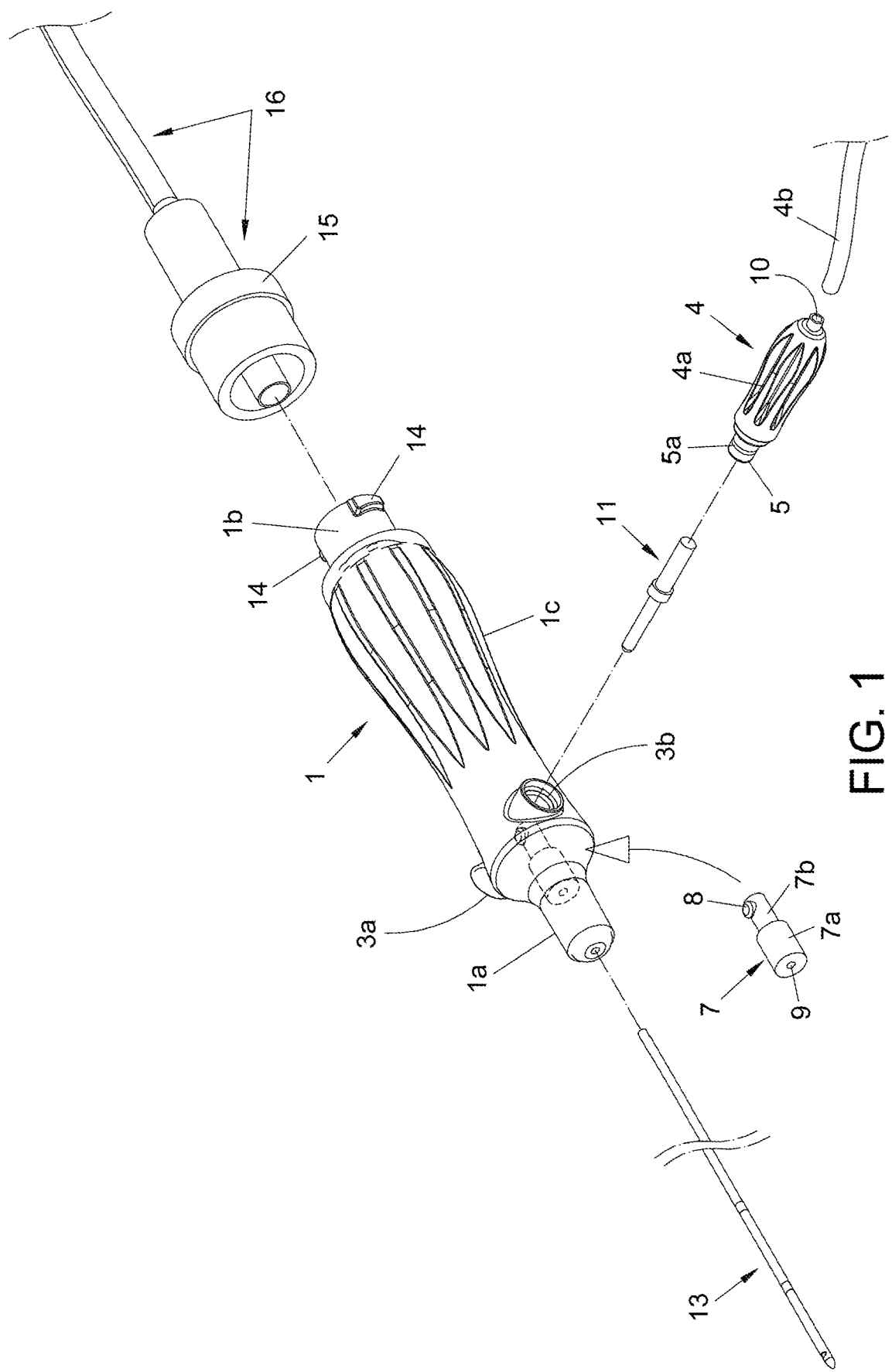
FIG. 1 shows an exploded perspective view of the needle device for a nerve block, object of the invention.
Figure 2:
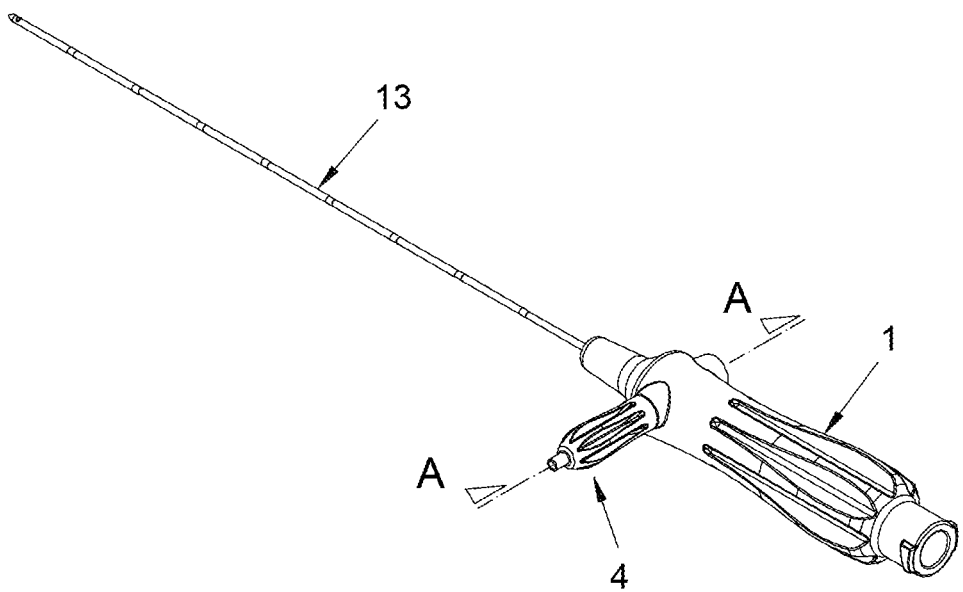
FIG. 2 shows a perspective view of the device of the invention.
Figure 3:
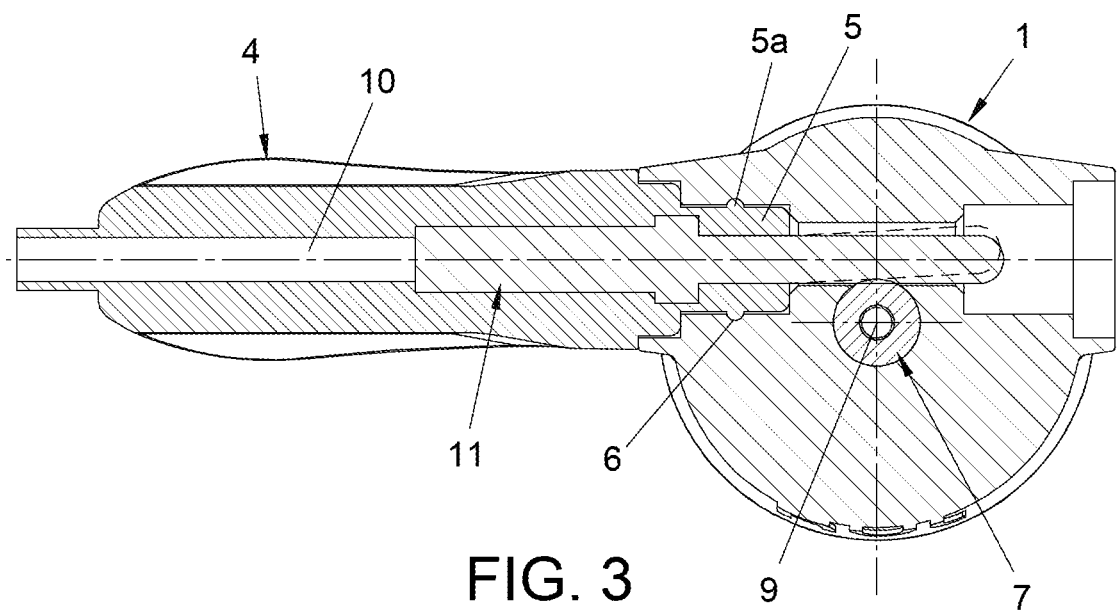
FIG. 3 shows an A-A cross-sectional view of FIG. 2.

Considering the numbering used in the figures, the needle device for a nerve block comprises a gripping part 1 with a revolution geometry that has a longitudinal passage 2 that intersects tangentially with the radial duct passage 3 that has two opposite female couplings 3a, 3b, into either of which the nerve stimulator 4 with an electrical signal can be inserted, depending on whether the user is left-handed or right-handed.

To this end, said nerve stimulator 4 is embedded inside one of said female couplings 3a, 3b by elastic pull thanks to an annular protrusion 5a incorporated in a male element 5 of an insertable head 4a of the nerve stimulator 4, wherein said annular protrusion 5a is complemented by one of the annular grooves 6 located inside the female couplings 3a, 3b.

The longitudinal passage 2 of the gripping part 1 has an anterior end section in accordance with a front portion 1a of the gripping part 1, where the female couplings 3a, 3b are located, and said longitudinal passage 2 has an outer end section in accordance with a rear portion 1b of the gripping part 1 opposite the front part 1a.

Housed inside the anterior end section of the longitudinal passage 2 is a cylindrical bushing 7 made of conductive material that has a radial nipple 8. Said cylindrical bushing 7 has an axial hole 9 and is made up of a first cylindrical body 7a with a greater diameter and a second cylindrical body 7b with a smaller diameter, which integrates the radial nipple. Said cylindrical bushing 7 is located in the confluence of the longitudinal passage 2 and radial duct passage 3.

The anterior end section of the longitudinal passage 2 has a narrowing 2a where a section of the needle 13 is inserted and adjusted, and where an end portion of said needle 13 is embedded and in turn fixed in the axial hole 9 of the cylindrical bushing 7.

The rear portion 1b of said gripping part 1 has two facing protrusions 14 in order to be able to couple an outer coupling 15 of a connecting tube 16 with axial and rotational retentions through which a liquid anesthesia fluid flows to the needle 13, wherein said end coupling 15 forms part of the connecting tube 16 assembly.

The insertable head 5 has a longitudinal hole 10 which has an end section where a deformable connector 11 is attached which has an outer portion that projects to the outside, wherein said outer portion perpendicularly and tightly connects to the radial nipple 8 of the cylindrical bushing 7 when nerve stimulator 4 is inserted to provide electric current to the needle 13 and thereby achieve the required stimulation of the nerves of the patient.

The deformable connector 11 protrudes to the outside through a front end of the insertable head 5, while the longitudinal hole 10 thereof opens at a rear end of the insertable head 5, through which a cable 4b is inserted that connects to the deformable connector 11 in order to provide an electrical signal to the cylindrical bushing 7, said cable 4b forming part of the nerve stimulator 4, as was previously mentioned.

The gripping part 1 comprises a centered outer section made up of a first grooved structure 1c formed by an alternating succession of longitudinal protrusions and channels so that the user is better able to grip said gripping part with their hand in a way that is safer, wherein said first grooved structure (1c) is situated between the first front portion (1a) and the rear portion (1b).

The insertable head 4a of the nerve stimulator 4 also has a revolution geometry with an outer section made up of a second grooved structure 12 formed by an alternating succession of longitudinal protrusions and channels, all of which is for improving the handling of said insertable head 4a and in general the device of the invention.

The invention claimed is:

1. A needle device for a nerve block, which comprises:
   a gripping part that has a longitudinal passage through which a liquid fluid flows, said liquid fluid also flowing through an inside of a needle aligned with said longitudinal passage; and
   a nerve stimulator, through which electric current is transmitted to the needle,
   wherein the gripping part comprises a radial duct that intersects tangentially with the longitudinal passage, the radial duct having two opposite female couplings into either of which the nerve stimulator can be inserted, depending on whether a user is left-handed or right-handed, and
   wherein housed inside an anterior end section of the longitudinal passage of the gripping part is a cylindrical bushing made of a conductive material, said cylindrical bushing being located in an area of confluence in which the longitudinal passage and the radial duct converge, and said cylindrical bushing having an axial hole into which an outer portion of the needle fits.

2. The needle device for a nerve block, according to claim 1, wherein the nerve stimulator includes a deformable connector with an outer portion that comes into contact with the cylindrical bushing in order to transmit electric current to the needle when said nerve stimulator is inserted into one of the female couplings of the gripping part.

3. The needle device for a nerve block, according to claim 2, wherein the cylindrical bushing includes a radial nipple with which the outer portion of the deformable connector of the nerve stimulator makes contact.

4. The needle device for a nerve block, according to claim 3, wherein the cylindrical bushing comprises a first cylindrical body with a greater diameter and a second cylindrical body with a smaller diameter, which integrates the radial nipple.

5. The needle device for a nerve block, according to claim 1, wherein the radial duct of the gripping part is located in a direction perpendicular to the direction of the longitudinal passage of the gripping part.

6. The needle device for a nerve block, according to claim 1, wherein the gripping part comprises a revolution geometry with a centered outer section made up of a first grooved structure formed by an alternating succession of longitudinal protrusions and channels.

7. The needle device for a nerve block, according to claim 1, wherein an anterior end section of the longitudinal passage of the gripping part has a narrowing where a section of the needle is adjusted, which is a continuation of the end portion of said needle embedded and fixed in the axial hole of the cylindrical bushing.

8. The needle device for a nerve block, according to claim 1, wherein the gripping part comprises a rear portion that has facing protrusions, where, in said rear portion, an outer coupling of a connecting tube through which the liquid fluid flows is coupled.

9. The needle device for a nerve block, according to claim 1, wherein the nerve stimulator comprises an insertable head that on one end has a male element that by an elastic pull is embedded inside one of the female couplings of the gripping part.

10. The needle device for a nerve block, according to claim 9, wherein the male element of the nerve stimulator has an annular protrusion that is complemented by an annular groove located inside the female couplings.

11. The needle device for a nerve block, according to claim 9, wherein the insertable head of the nerve stimulator has a revolution geometry with an outer section made up of a second grooved structure formed by an alternating succession of longitudinal protrusions and channels.

* * * * *